United States Patent
Irisawa

[11] Patent Number: 5,885,249
[45] Date of Patent: Mar. 23, 1999

[54] SYRINGE WITH CAP

[75] Inventor: Masahiro Irisawa, Yokohama, Japan

[73] Assignee: NIFCO Inc., Yokohama, Japan

[21] Appl. No.: 628,801

[22] Filed: Apr. 5, 1996

[30]     Foreign Application Priority Data

Apr. 6, 1995  [JP]  Japan ................................. 7-081266
 Apr. 12, 1995 [JP]  Japan ................................. 7-087257

[51] Int. Cl.⁶ .................................................. A61M 5/00
[52] U.S. Cl. ......................... 604/111; 604/192; 604/263
[58] Field of Search ........................... 128/919; 604/192, 604/263, 110, 187, 198, 181, 111

[56]            References Cited

U.S. PATENT DOCUMENTS 4,982,842  1/1991  Hollister ................................ 604/263
 5,151,089  9/1992  Kirk, III et al. ....................... 604/192
 5,152,751  10/1992 Kozlowski ............................. 604/192
 5,490,841  2/1996  Landis .................................. 604/192
 5,599,313  2/1997  Gyure et al. .......................... 604/111
 5,662,617  9/1997  Odell et al. ........................... 128/919

*Primary Examiner*—Ronald Stright, Jr.
*Attorney, Agent, or Firm*—Kubovcik & Kubovcik

[57]            ABSTRACT

Disclosed is a syringe with a cap including a syringe main body (30) having a needle attached to the extreme end thereof and the cap (40) for covering the needle (20) of the syringe main body (30), wherein the cap (40) includes a cap securing portion (50) secured to the extreme end of the syringe main body (30) and a cap main body (70) pivotally coupled with the cap securing portion (50) through a hinge portion (60) and the cap main portion (70) includes an accommodating portion for accommodating the needle (20) and a cut-out portion (72) which communicates with the accommodating portion and into which the needle (20) can go in and from which the needle can be taken out, the syringe with cap comprising securing elements (52, 73, 80) capable of securing the cap to the cap securing portion (50) when the syringe is used.

7 Claims, 11 Drawing Sheets

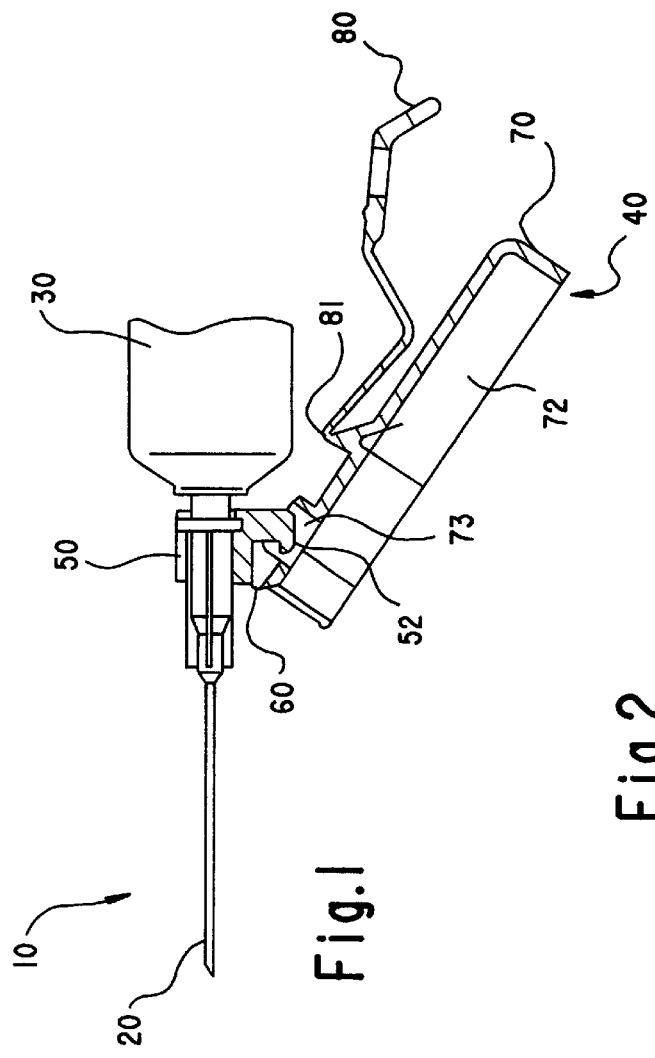
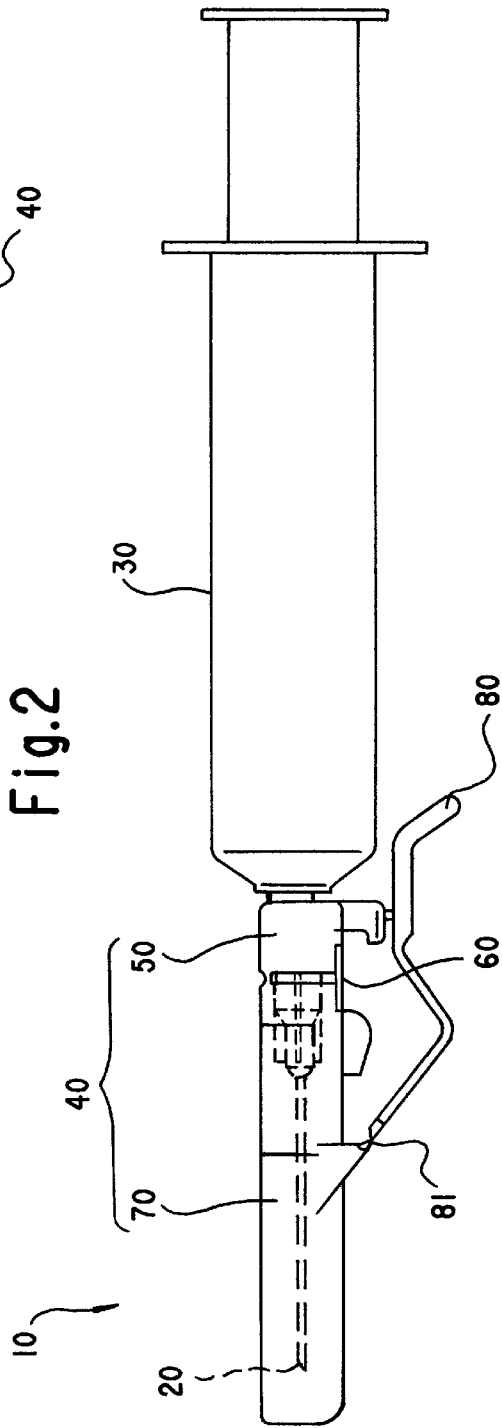
Fig.1
Fig.2

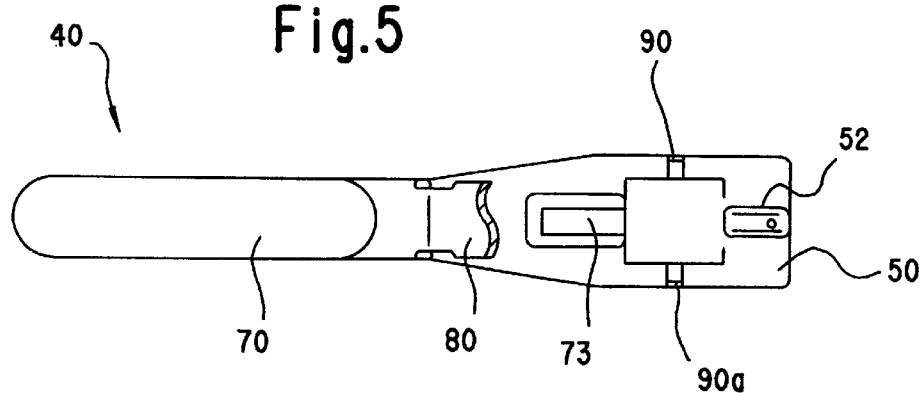
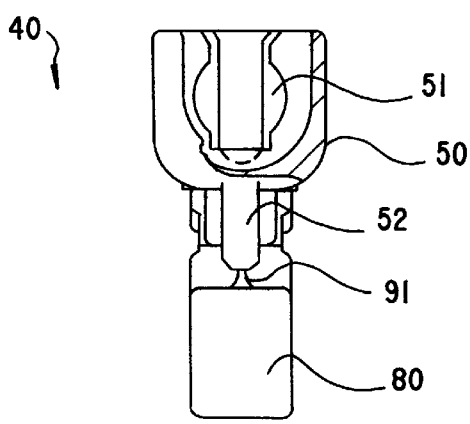
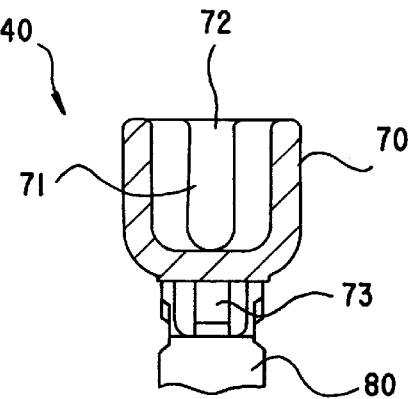
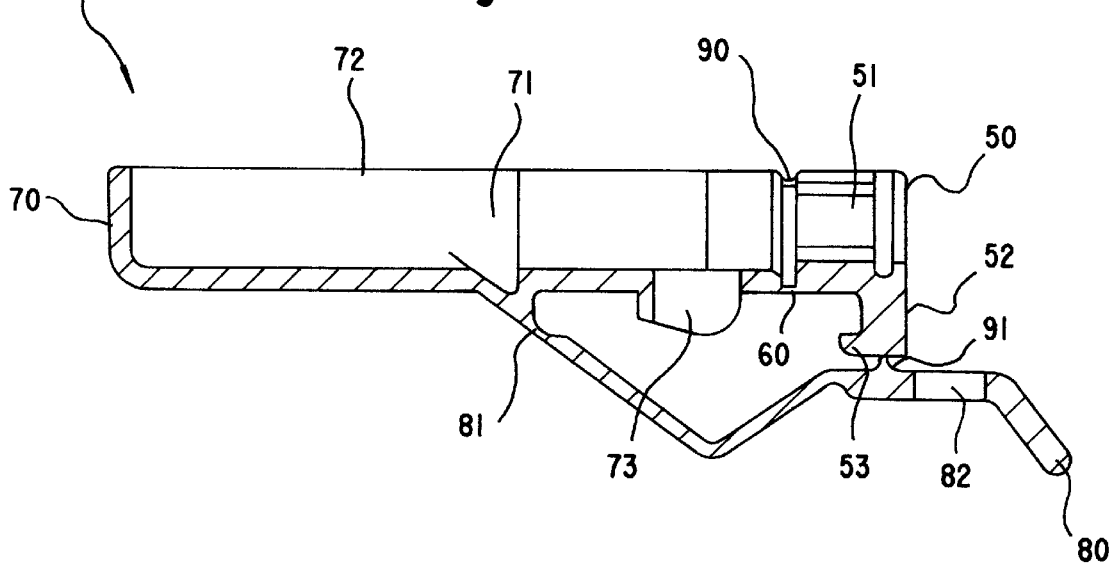

SYRINGE WITH CAP

BACKGROUND OF THE INVENTION AND DESCRIPTION OF THE RELATED ART

The present invention relates to a syringe with a cap, and more specifically, to a syringe with a cap capable of securely locking the cap at an open position and a closed position Conventionally, there is known a syringe including a syringe main body having a needle mounted at the extreme end thereof and a cap for covering the needle of the syringe main body as this type of the syringe (for example, Japanese Utility Model Application Laid-Open No. Sho 63-189255, Japanese Utility Model Application Laid-Open No. Sho 64-17248, Japanese Utility Model Application Laid-Open No. Hei 1-62849 and the like).

The aforesaid conventional cap includes a cap securing portion secured at the extreme end of the syringe main body and a cap main body pivotally coupled with the cap securing portion though a hinge portion.

The aforesaid conventional cap main body includes an accommodating portion for accommodating a needle and a cut-out portion which communicates with the accommodating portion and into which the needle can go and from which the needle can be taken out.

However, the aforesaid conventional syringe has a first problem that when an injection is effected by opening the cap by turning it on the hinge portion, the cap swings from the hinge portion and disturbs medical treatment.

Further, there is a second problem that when the cap is closed by being turned in a reverse direction on the hinge portion after the syringe is used, since the syringe has the same outside appearance as that of an unused syringe, it cannot be determined whether or not the needle is already used.

OBJECT AND SUMMARY OF THE INVENTION

Taking the above problems into consideration, an object of the present invention is to provide a syringe with a cap capable of preventing the swinging of the cap when the syringe is used.

Another object of the present invention is to be able to determine whether a needle is not yet used or already used from the outside appearance thereof in the state that the needle is covered with the cap.

Still another object of the present invention is to be able to more securely determine whether a needle is not yet used or already used.

A further object of the present invention is to prevent a used needle from being unnecessarily exposed from a cap.

According to the present invention for achieving the above objects, there is provided a syringe with a cap including a syringe main body having a needle attached to the extreme end thereof and the cap for covering the needle of the syringe main body, wherein the cap includes a cap securing portion secured to the extreme end of the syringe main body and a cap main body pivotally coupled with the cap securing portion through a hinge portion and the cap main body includes an accommodating portion for accommodating the needle and a cut-out portion which communicates with the accommodating portion and into which the needle can go and from which the needle can be taken out, the aforesaid syringe with cap comprising securing means capable of securing the cap to the cap securing portion when the syringe is used.

Therefore, in the present invention, the syringe can be used in the state that the cap is secured.

The present invention includes a locking means which is interposed between the cap securing portion and the cap main body and locks the cap main body to the cap securing portion at a position for use where the needle is exposed by turning the cap main body from an accommodating position where the needle is accommodated in the accommodating portion of the cap main body on the hinge portion.

Therefore, according to the present invention, the cap main body is turned on the hinge portion and exposes the needle from the state that the needle is covered with the cap. The cap main body is secured to the cap securing portion by the locking means in use at the position for use so that the swing of the cap main body is prevented.

The present invention includes a locking means in disposal which is interposed between the cap securing portion and the cap main body for turning the cap main body in a reverse direction from the position for use where the needle is disposed on the hinge portion to thereby accommodate the used needle to the accommodating portion and locking the cap main body to the cap securing portion at a position for disposal different from the accommodating position.

Therefore, according to the present invention, after the needle is used, the cap main body is turned in the reverse direction on the hinge portion to thereby accommodate the used needle in the accommodating portion of the cap main body.

At the time, the cap main body is secured, for example, by the locking means in disposal at the position for disposal different from the accommodating position with respect to the cap fixing portion.

As a result, whether the needle is already used or it is not yet used can be determined by observing the state of the needle accommodated in the cap main body. In addition to the above, since the cap main body is secured to the cap securing portion by the locking means in disposal, there is no possibility that the used needle is carelessly exposed.

The present invention includes a breakable breaking portion which is interposed between the cap securing portion and the cap main body at the position where the unused needle is accommodated in the accommodating portion of the cap main body to secure the cap main body to the cap securing portion.

That is, the needle can be made to a usable state when it is exposed by breaking the breaking portion and turning the cap main body on the hinge portion.

As a result, whether the needle is already used or it is not yet used can be determined by observing the state of the breaking portion. In addition to the above, since the cap main body is secured to the cap securing portion through the breaking portion when the needle is not yet used, there is no possibility that the needle is carelessly exposed, thus the needle can be kept in a safe and sanitary state.

The present invention includes a spring means which is interposed between the cap securing portion and the cap main body, the spring means urging the cap main body toward a direction for securing the cap main body to the cap securing portion at the position for use where the needle is exposed by turning the cap main body on the hinge portion as well as urging the cap main body toward a position where the needle is located in the accommodating portion when the cap main body is turned in the reverse direction on the hinge portion.

Thus, according to the present invention, when the cap main body is turned toward an open direction on the hinge portion against the urging force of the spring means from an unused state, the needle is exposed to the outside through the cut-out portion of the cap main body.

At the position for use where the needle is exposed, the urging direction of the spring means is reversed so that the cap main body is urged toward the cap securing portion by the urging force of the spring means. As a result, the cap main body can be prevented from being carelessly swung when the needle is used.

When the cap main body is turned toward a close direction on the hinge portion against the urging force of the spring means after the needle is used, the used needle is accommodated in the accommodating portion of the cap main body.

At the time, the urging direction of the spring means is reversed so that the cap main body is urged toward the position where the used needle is located in the accommodating portion by the urging force of the spring means.

As a result, it can be prevented that the cap main body is carelessly opened and the used needle is exposed.

In the present invention, the interior of the accommodating portion of the cap main body is divided into two portions of a vacant accommodating portion used when needle is not used which faces to the cut-out portion and accommodates the unused needle and a vacant accommodating portion used when needle is disposed of which communicates with the above vacant accommodating portion and accommodates the needle after it is used and the accommodating portion forms a projection projecting therein.

Consequently, in the present invention, the unused needle is accommodated in the vacant accommodating portion used when needle is not used of the cap main body. Since the vacant accommodating portion used when needle is not used faces to the cut-out portion, the cap main body can be promptly released.

On the other hand, the used needle gets into the vacant accommodating portion used when needle is not used through the cut-out of the cap main body. Next, the used needle further goes to an inner part while avoiding the projection projecting in the accommodating portion and is accommodated in the vacant accommodating portion used when needle is disposed of.

As a result, since the used needle is located in the inner part of the accommodating portion, even if the cap main body is turned toward the open direction on the hinge portion, it is abutted against the projection and the careless exposure thereof to the outside can be prevented.

Further, since the needle, when it is already used, is accommodated in the position different from that where the needle is accommodated when it is not yet used, whether the needle is already used or not yet used can be easily determined from the outside appearance thereof.

Further, the present invention includes a spring means which is formed between the cap securing portion and the cap main body, the spring means urging the cap main body toward a direction for securing the cap main body to the cap securing portion at the position for use where the needle is exposed by turning the cap main body on the hinge portion as well as urging the cap main body toward a position where the used needle is located in the vacant accommodating portion used when needle is disposed of when the cap main body is turned in a reverse direction on the hinge portion.

BRIEF DESCRIPTION OF THE DRAWINGS

FIG. 1 is a view, partly in cross section, of a portion of a syringe in the state that a cap main body is locked to a position for use;

FIG. 2 is a plan view of an unused syringe;

FIG. 3 to FIG. 8 show an unused cap, respectively, wherein:

FIG. 4 is an upper plan view of the cap of FIG. 3;

FIG. 5 is a bottom plan view showing the state that the cap main body of FIG. 3 is partly broken;

FIG. 6 is a side elevational view showing the state that the cap main body of FIG. 3 is partly broken;

FIG. 7 is a cross sectional view along the line VII—VII of FIG. 3; and

FIG. 8 is a cross sectional view along the line VIII—VIII of FIG. 4;

FIG. 11 and FIG. 12 show the state that the cap main body is locked to a disposing position, respectively, wherein:

FIG. 11 is plan view of a portion of the syringe; and

FIG. 12 is a longitudinal cross sectional view of the cap of FIG. 11;

FIG. 18 to FIG. 22 show a cap in a molding process, wherein:

FIG. 18 is a plan view of the cap;

FIG. 19 is a bottom plan view of the cap of FIG. 18;

FIG. 20 is a cross sectional view along the line V—V of FIG. 19;

FIG. 21 is a left side elevational view of the cap of FIG. 18;

FIG. 22 is a right side elevational view of the cap of FIG. 18;

FIG. 23 and FIG. 24 show accommodating positions of a needle, wherein:

FIG. 23 is a cross sectional view of a cap main body showing the accommodating position of an unused needle;

FIG. 24 is a cross sectional view of the cap main body showing the accommodating portion of a used needle;

Figure 3:
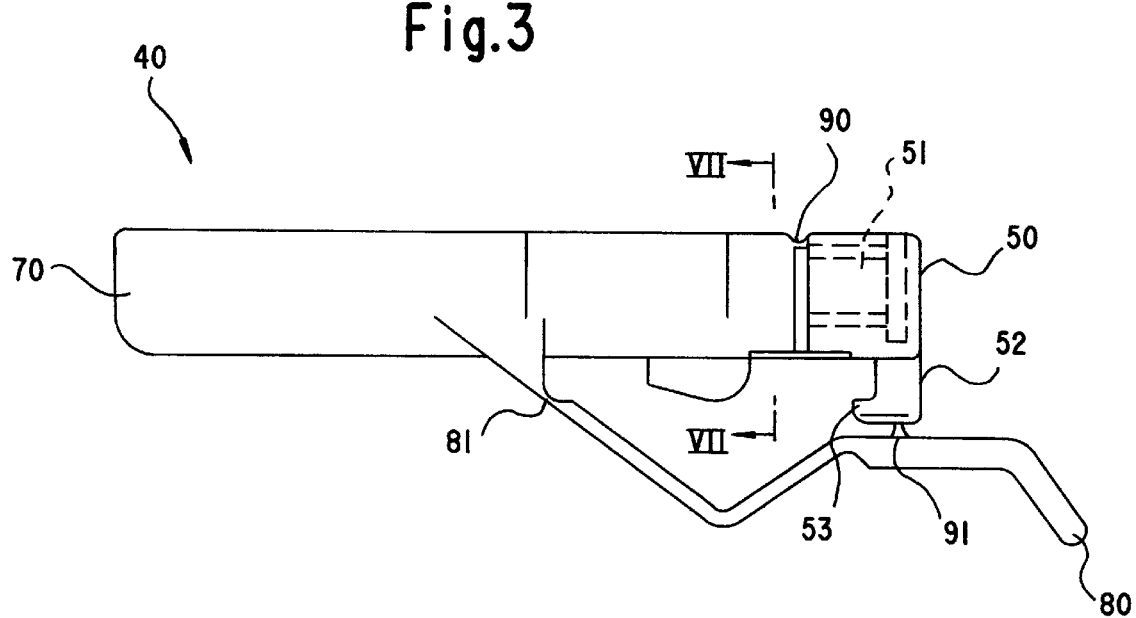

DESCRIPTION OF PREFERRED
EMBODIMENTS OF THE INVENTION

FIG. 1 to FIG. 11 show a first embodiment of the present invention.

FIG. 2 denotes a medical syringe 10 which includes, a syringe main body 30 having a needle 20 mounted at the extreme end thereof and a cap 40 covering the needle 20 of the syringe main body 30.

As shown in FIG. 2, the cap 40 includes a cap securing portion 50 secured at the extreme end of the syringe main body 30 and a cap main body 70 pivotally coupled with the cap securing portion 50 through a hinge portion 60, when they are further roughly classified. The cap 40 is molded from thermoplastic synthetic resin such as, for example, PP and the like having suitable rigidity and elasticity as a integral unit and subjected to sterilizing treatment after it is molded.

As shown in FIG. 6 and FIG. 8, the cap securing portion 50 is molded to a hollow cylindrical shape and has a mounting portion 51 formed thereinto, the mounting portion 51 having a C-shaped cross section with its upper surface opened so that the extreme end of the syringe main body 30 fits thereinto. The extreme end of the syringe main body 30 is mounted from the upper open surface of the mounting portion 51 making use of the elasticity of resin and the mounting portion 51 secured to the extreme end of the syringe main body 30 making use of the restoring force of resin.

As shown in FIG. 8 the hinge portion 60 has a thin wall structure and couples the lower end of the cap securing portion 50 with the lower end of the cap main body 70.

As shown in FIG. 7 and FIG. 8, the cap main body 70 includes an accommodating portion 71 for accommodating the needle 20 and a cut-out portion 72 which communicates with the accommodating portion 71 and into and from which the needle 20 can go and out.

As shown in FIG. 7 and FIG. 8 the cap main body 70 is formed to a hollow rectangular shape, the upper portion of which is open in the longitudinal direction, and the entire length thereof is set longer than the needle 20.

More specifically, the cap main body 70 has a groove formed to the interior thereof as shown in FIG. 7 and FIG. 8, the groove having an U-shaped cross section with its upper surface opened. The groove has a width set greater than the diameter of the needle 20 as well as an entire length set longer than the needle 20. The interior of the groove of the cap main body 70 is arranged as the accommodating portion 71 for accommodating the needle 20 and the open upper surface of the groove is arranged as the cut-out portion 72 into and from which the needle 20 can and out. Further, the cut-out portion 72 is formed to an elliptical shape having a major axis in the axial direction of the needle 20 as shown in FIG. 4.

On the other hand, the cap main body 70 includes an operating handle 80 used for opening and closing operation as shown in FIG. 3 and FIG. 8 and an end of the operating handle 80 is coupled with the bottom surface of the cap main body 70 through a thin wall portion 81.

As shown in FIG. 8, two breakable breaking portions 90, 91 are formed between the cap securing portion 50 and the cap main body 70.

Figure 4:
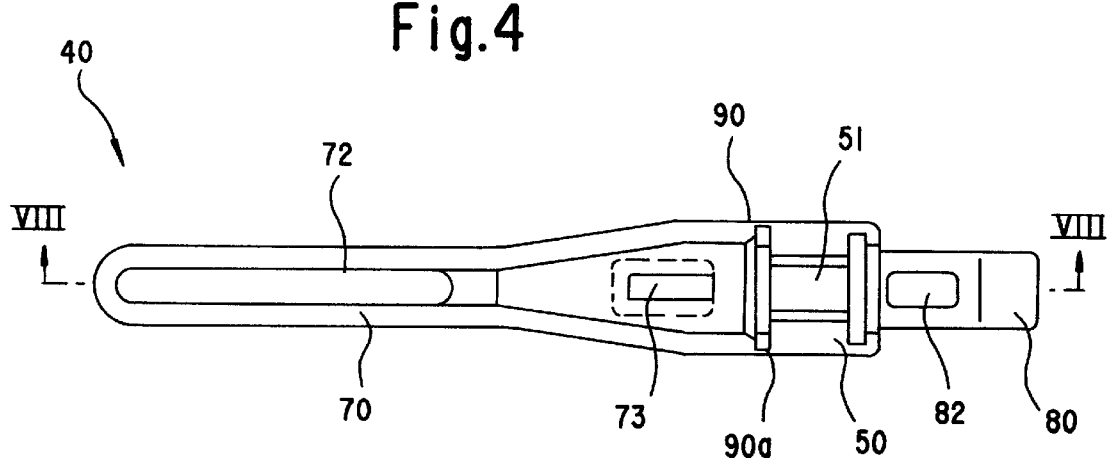

As shown in FIG. 4 and FIG. 8, the first breaking portion 90, which is used to couple the upper end of the cap securing portion 50 with the upper end of the cap main body 70, is formed to a pair 90a and 90 on the right and left sides, respectively and has a thin wall structure.

As shown in FIG. 6 and FIG. 8, the second breaking portion 91 is formed between the cap securing portion 50 and the operating handle 80 and has a thin wall structure. The cap securing portion 50 and the cap main body 70 are coupled with each other through the operating handle 80 having the second breaking portion 91.

Note, although the breaking portions 90, 91 are formed at two positions in the embodiment shown in the drawings, they may be formed at one position or at three or more positions.

As shown in FIG. 8, there is provided a locking means in use and a locking means in disposal between the cap securing portion 50 and the cap main body 70. The locking means in use locks the cap main body 70 to the cap securing portion 50 at the position for use (refer to FIG. 1) where the needle 20 is exposed by turning the cap main body 70 from an accommodating position (refer to FIG. 2) where the needle 20 is accommodated in the accommodating portion 71 of the cap main body 70 on the hinge portion 60. The locking means in disposal turns the cap main body 70 in a reverse direction from the position for use (refer to FIG. 1) where the needle 20 is exposed on the hinge portion 60 to thereby accommodate the used needle 20 to the accommodating portion 71 and locks the cap main body 70 to the cap securing portion 50 at a position for disposal (refer to FIG. 11 and FIG. 12) different from the accommodating position (refer to FIG. 2).

First, the locking means in use is composed of a locking projection 52 projecting from the bottom of the cap securing portion 50 downward and a locking groove 73 which is formed on the bottom of the cap main body 70 and into which the locking projection 52 fits, as shown in FIG. 1 and FIG. 8.

The extreme end of the locking projection 52 includes a hook portion 53 projecting in an L-shape toward the extreme end of the needle 20 as shown in FIG. 8. Further, the aforesaid second breaking portion 91 is formed to the lower end of the hook portion 53 which is continued to the operating handle 80 through the breaking portion 91 when molded.

The locking groove 73 is formed to a long rectangular shape in the axial direction of the needle 20 and the right to left width of the groove is set less than the thickness of the locking projection 52 as shown in FIG. 5. Therefore, the locking projection 52 is inserted into the locking groove 73 making use of the elasticity of resin and held therein by the elastic restoring force and frictional force of resin.

Note, although the locking projection 52 is formed to the cap securing portion 50 and the locking groove 73 is formed to the cap main body 70, respectively in the embodiment shown in the drawings, the locking groove may be formed to the cap securing portion 50 and the locking projection may be formed to the cap main body 70, respectively.

Figure 12:
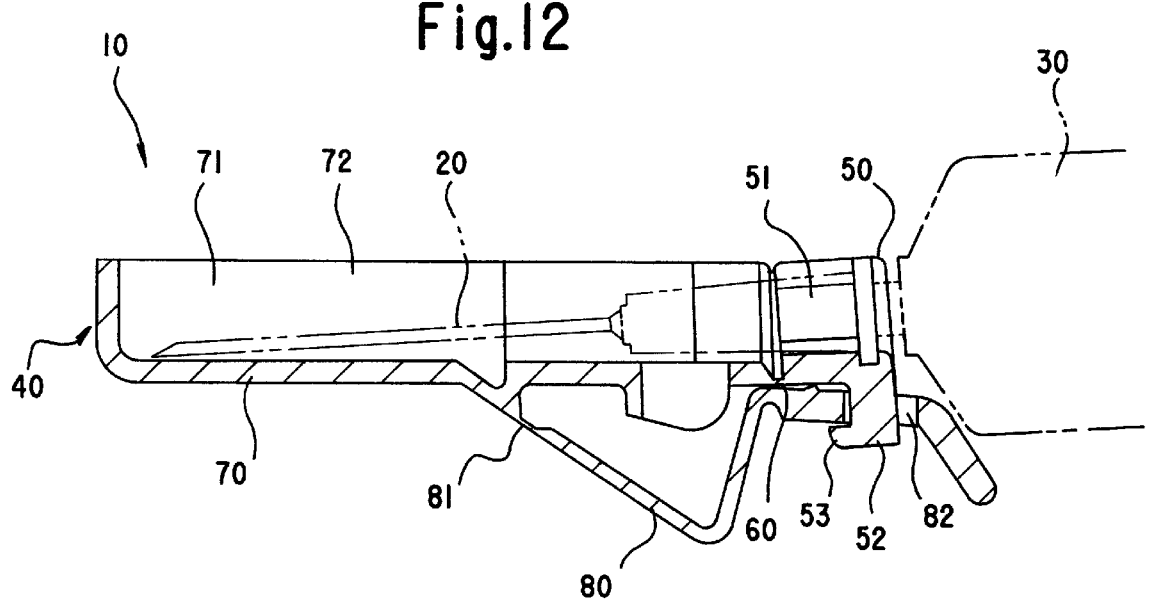

As shown in FIG. 8 and FIG. 12, the locking means in disposal is composed of the above locking projection 52 formed to the cap securing portion 50 and a locking hole 82 which is formed at an intermediate position of the operating handle 80 in the lengthwise direction thereof and into which the locking projection 52 fits.

As shown in FIG. 4, the above locking hole 82 is formed to a long rectangular shape in the axial direction of the needle 20 likewise the locking groove 73 of the cap main body 70. Further, it suffices only to set the right to left groove width of the operating handle 80 less than the thickness of the locking projection 52. Thus, the locking hole 82 cannot be removed from the locking projection 52 in such a manner that the hook portion 53 of the locking projection 52 inserted into the locking hole 82 is hooked to the edge of the locking hole 82.

Note, the locking hole 82 may be arranged to a structure similar to that of the locking groove 73 and use the elastic restoring force and frictional force of resin.

Although the locking projection 52 is formed to the cap securing portion 50 and the locking hole 82 is formed to the operating handle 80, respectively in the embodiment shown in the drawings, the locking hole may be formed to the cap securing portion 50 and the locking projection may be formed to the operating handle 80, respectively on the contrary. Further, it is sufficient only to form one of concave/convex portions which are engaged with each other to the cap securing portion 50 and the other of them to one or both of the cap main body 70 and the operating handle 80 thereof, respectively as the locking means at disposal.

Next, a sequence for using the cap 40 arranged as described above will be described.

First, the syringe main body 30 is mounted to the mounting portion 51 of the cap securing portion 50 as shown in FIG. 2 as well as when the needle 20 is not yet used, the cap main body 70 is secured to the cap securing portion 50 through the first breaking portion 90. Further, the cap main body 70 is secured to the cap securing portion 50 through the second breaking portion 91 of the operating handle 80.

As a result, when the first and second breaking portions 90, 91 are not broken, it can be easily determined that the needle 20 is not yet used from the outside view thereof.

Since the unused needle 20 is accommodated in the accommodating portion 71 of the cap main body 70 as shown in FIG. 2, it is in a safe and sanitary state.

Further, since the cap main body 70 is coupled with the cap securing portion 50 through the first and second breaking portions 90, 91, the cap main body 70 is also prevented from being carelessly opened.

Figure 9:
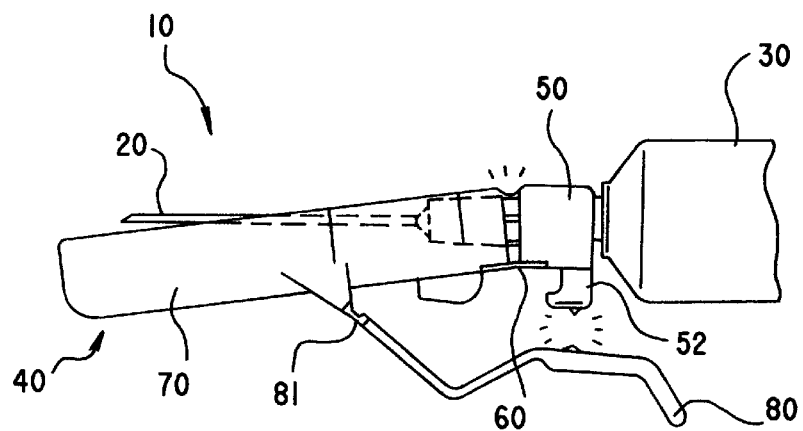
FIG. 9 is a cross sectional view of a portion of the syringe showing the state that the breaking portion of the cap is broken.

Next, when the needle 20 is to be used, it suffices only to bend the cap main body 70 downward while holding it as shown in FIG. 9.

When the cap main body 70 is bent downward, the first and second breaking portions 90, 91 are broken as shown in, for example, FIG. 9.

Next, it is sufficient only to pull the operating handle 80 of the cap main body 70 toward the direction of the syringe main body 30 while holding the operating handle 80.

Figure 10:
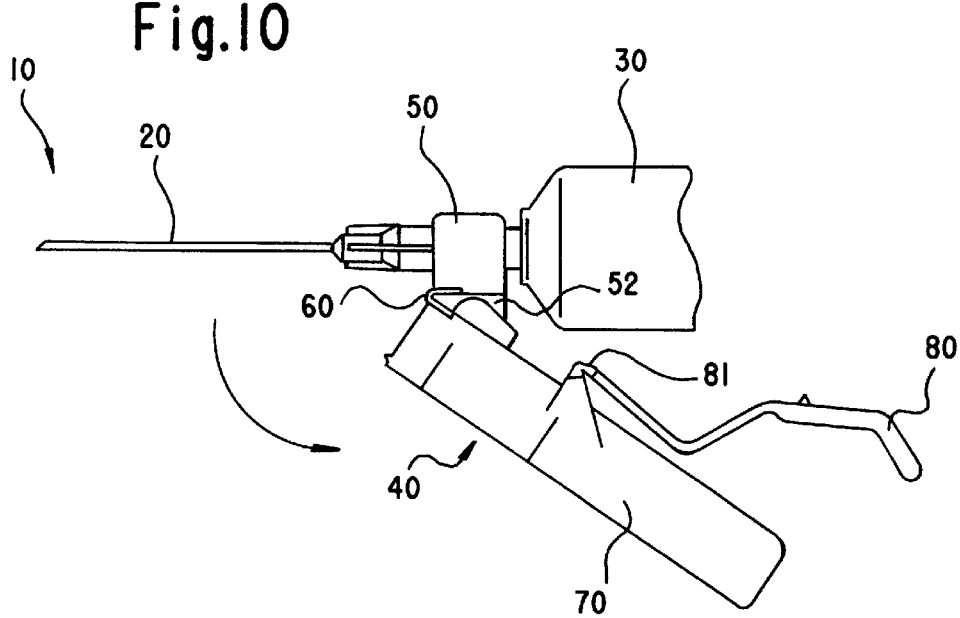
FIG. 10 is a plan view of a portion of the syringe showing the state that the cap main body is locked to a position for use.

When the operating handle 80 is pulled as described above, the cap main body 70 turns on the hinge portion 60 as shown in FIG. 1 and FIG. 10. At the time, the needle 20 slips out from the accommodating portion 71 through the cutout portion 72 of the cap main body 70.

When the operating handle 80 is further pulled, the locking groove 73 of the cap main body 70 is locked to the locking projection 52 of the cap securing portion 50.

When the operating handle 80 is further pulled strongly at the time, the groove width of the locking groove 73 of the cap main body 70 is widened by the elastic force of resin by being pressed by the locking projection 52 of the cap securing portion 50, so that the locking projection 52 fits into the locking groove 73 in a confined state.

As a result, the cap main body 70 is locked to the cap securing portion 50 to thereby prevent the swing of the cap main body 70 when the exposed needle 20 is used.

After the needle 20 is used, it suffices only to press the operating handle 80 toward the tip direction of the needle 20 while holding the operating handle 80.

Figure 11:
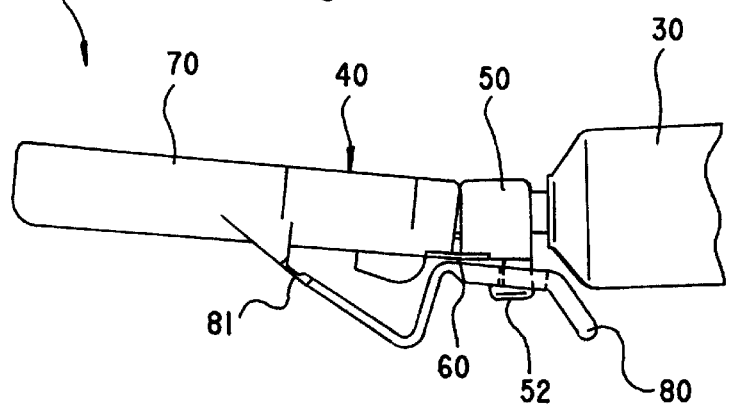

When the operating handle 80 is pressed, the cap main body 70 turns in the reverse direction on the hinge portion 60 as shown in FIG. 11 and FIG. 12. At the time, the used needle 20 gets into the accommodating portion 71 again through the cut-out portion 72 of the cap main body 70.

Then, the tip of the used needle 20 is abutted against the bottom of the cap main body 70 and the turn of the cap main body 70 is stopped.

When the operating handle 80 is further pressed, the operating handle 80 is bent to an approximately V-shape by the elastic force of resin and the position of the locking hole 82 of the operating handle 80 coincides with the position of the locking projection 52 of the cap securing portion 50 as shown in FIG. 12.

When the operating handle 80 is pressed upward at the time, the locking projection 52 gets into the locking hole 82 as shown in FIG. 12.

Subsequently, when the pressure force for pressing the operating handle 80 is released, the operating handle 80 bent to the approximately V-shaped is somewhat extended by the restoring force of resin. At the time, the position of the locking hole 82 relatively retracts a little. As a result, when the operating handle 80 tends to come off downward, the locking hole 82 cannot come off from the locking projection 52 because the hook portion 53 of the locking projection 52 is hooked to the edge of the locking hole 82.

Therefore, the cap main body 70 is locked to the cap securing portion 50, so that the cap main body 70 is prevented from being carelessly opened as shown in FIG. 12.

Since the cap main body 70 is in the upwardly bent state with respect to the cap securing portion 50 as shown in FIG. 12, it can be easily determined that the cap main body 70 is already used from the outside appearance thereof.

Further, the existence of the operating handle 80 prevents a hand from getting in touch with the vicinity of the tip of the used needle 20 or the tip from facing toward the direction of an operator. Thus, there is no possibility that the needle tip erroneously pierces or comes into contact with the hand of the operator and the needle is in a safe and sanitary state.

Figure 13:
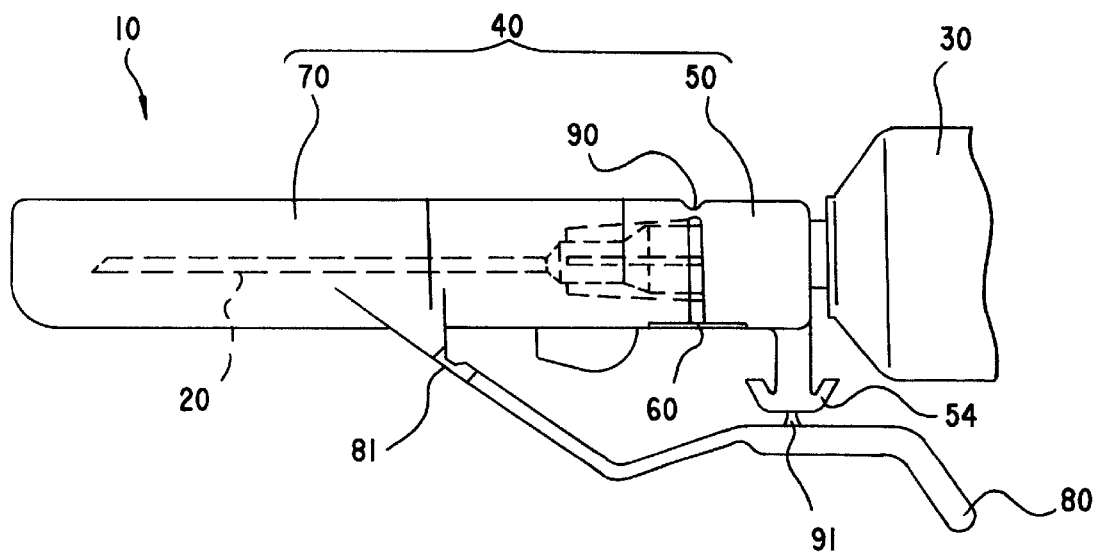
FIG. 13 showing a second embodiment of the present invention is a plan view of a portion of an unused syringe.
Figure 14:
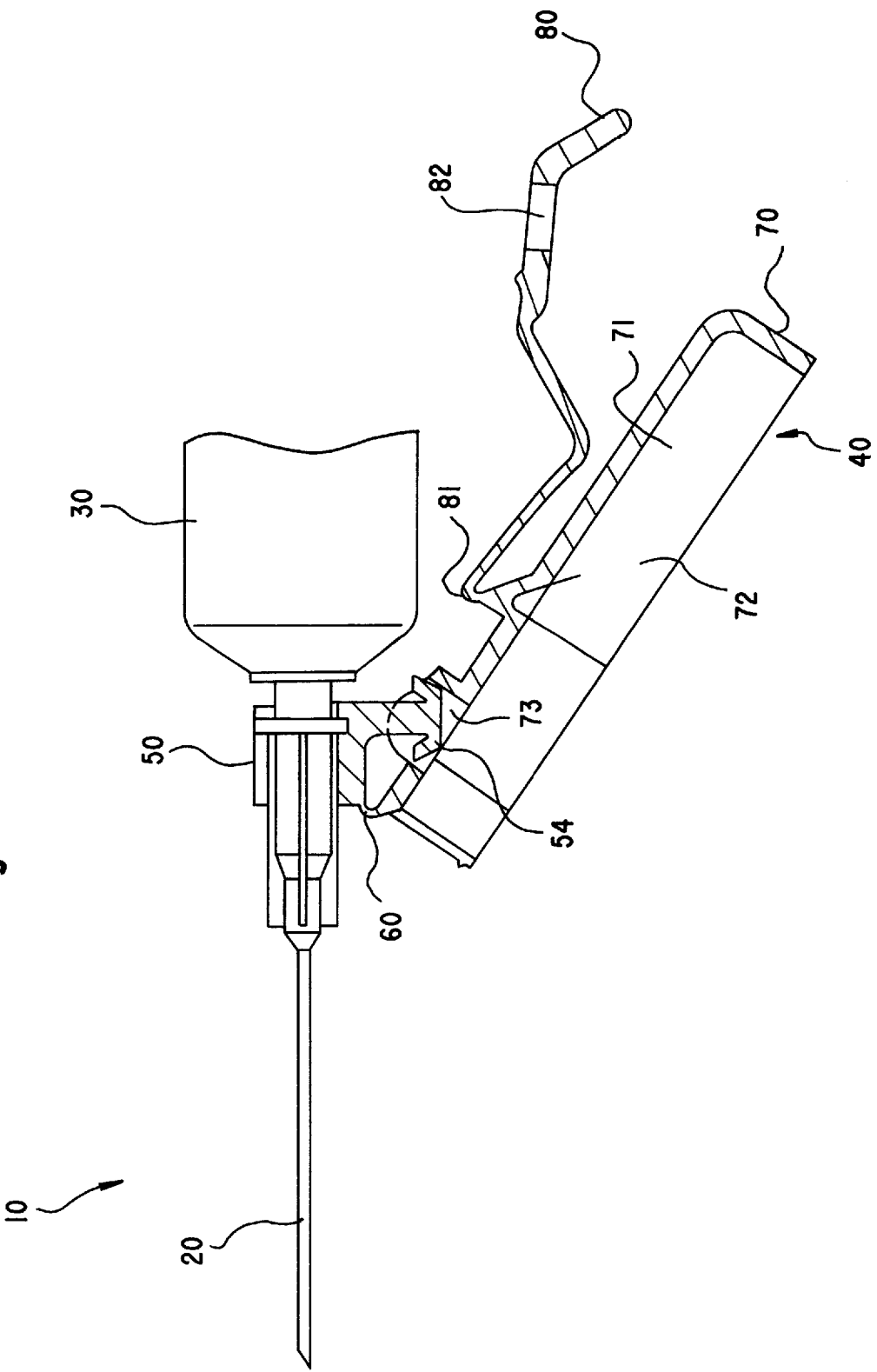
FIG. 14 is a view, partly in cross section, of a portion of the syringe showing the state that a cap main body of FIG. 13 is locked to a position for use.
Figure 15:
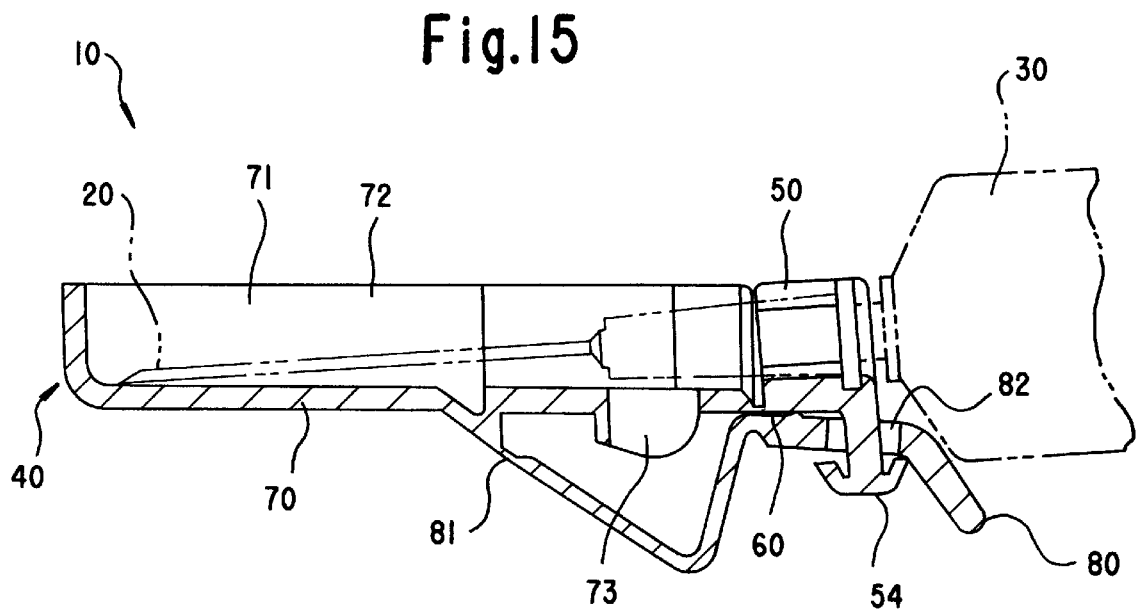
FIG. 15 is a view, partly in cross section, of a portion of the syringe showing the state that the cap main body of FIG. 13 is locked to a disposal position.

FIG. 13 to FIG. 15 show a second embodiment of the present invention, wherein FIG. 13 is a plan view of a portion of an unused syringe, FIG. 14 is a view, partly in cross section, of a portion of the syringe of FIG. 13 showing the state that a cap main body is locked to a position for use and FIG. 15 is a view, partly in cross section, of a portion of the syringe of FIG. 13 showing the state that the cap main body of FIG. 13 is locked to a position for disposal.

As shown in FIG. 13 to FIG. 15, the second embodiment forms a locking projection 54 of a cap securing portion 50 to an anchor shape.

That is, a locking hole 82 of an operating handle 80 is formed a little smaller than the locking projection 54 of the cap securing portion 50.

Note, in the description of the second embodiment, portions arranged similarly to those of the first embodiment described previously are denoted by the numerals and the description thereof is omitted.

With this arrangement, when the locking projection 54 of the cap securing portion 50 is inserted into the locking hole 82 of the operating handle 80 after a needle 20 is used as shown in FIG. 15, the locking projection 54 passes through the locking hole 82 by being pressed by the edge of the locking hole 82 while being narrowed by the elastic force of resin. When the locking projection 54 has passed through the locking hole 82, it is expanded by the restoring force of resin and cannot slip out from the locking hole 82.

As a result, according to the second embodiment, the removal from the locking projection 54 of the cap securing portion 50 can be made more difficult.

Note, although the locking projection 54 of the cap securing portion 50 is formed to an anchor shape in the second embodiment, it is not limited thereto and may be formed to a canoe shape.

Next, a third embodiment according to the present invention will be described.

Figure 17:
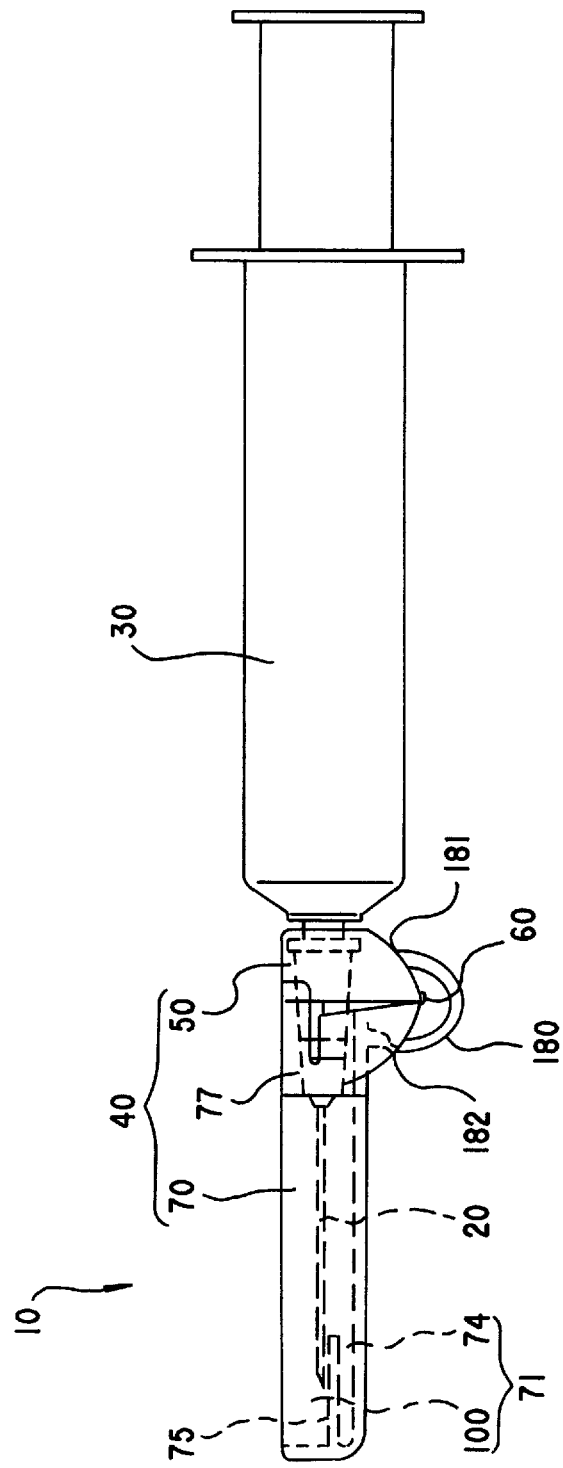
FIG. 17 is a plan view of the syringe showing the state that the cap main body is opened.

In FIG. 17, numeral 10 denotes a medical syringe which includes, a syringe main body 30 having a needle 20 mounted at the extreme end thereof and a cap 40 covering the needle 20 of the syringe main body 30.

As shown in FIG. 17, the cap 40 includes a cap securing portion 50 secured to the extreme end of the syringe main body 30 and a cap main body 70 pivotally coupled with the cap securing portion 50 through a hinge portion 60. The cap 40 is molded from thermoplastic synthetic resin such as, for example, polypropylene and the like having suitable rigidity and elasticity as a integral unit and subjected to sterilizing treatment after it is molded.

Figure 20:
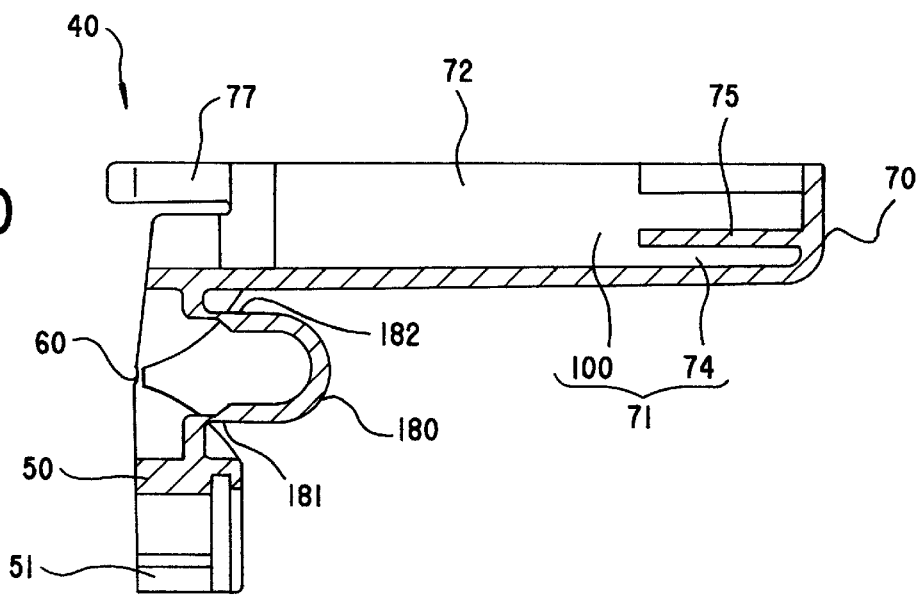
Figure 21:
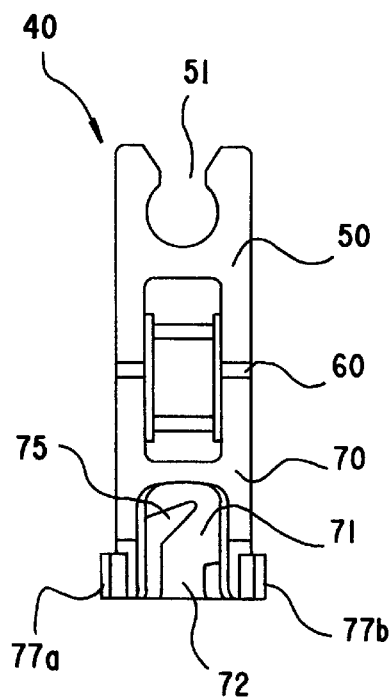
Figure 22:
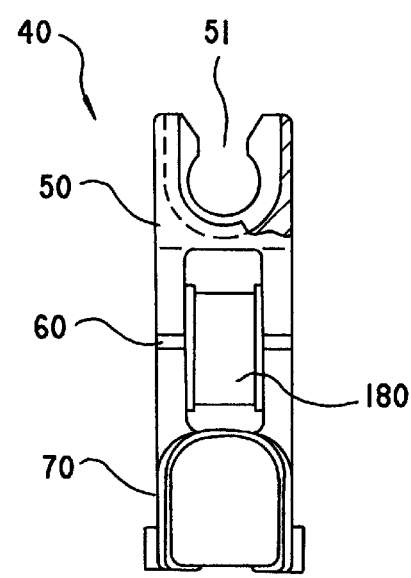

As shown in FIG. 20 to FIG. 22, the cap securing portion 50 is molded to a hollow cylindrical shape and the interior of the cap securing portion 50 has a mounting portion 51 formed thereto, the mounting portion 51 having a C-shaped cross section with its upper surface opened so that the extreme end of the syringe main body 30 fits thereinto. The syringe main body 30 is mounted to the mounting portion 51 from the upper open surface thereof making use of the elasticity of resin of the extreme end of the syringe main body 30 and the mounting portion 51 is secured to the extreme end of the syringe main body 30 making use of the restoring force of resin.

Figure 18:
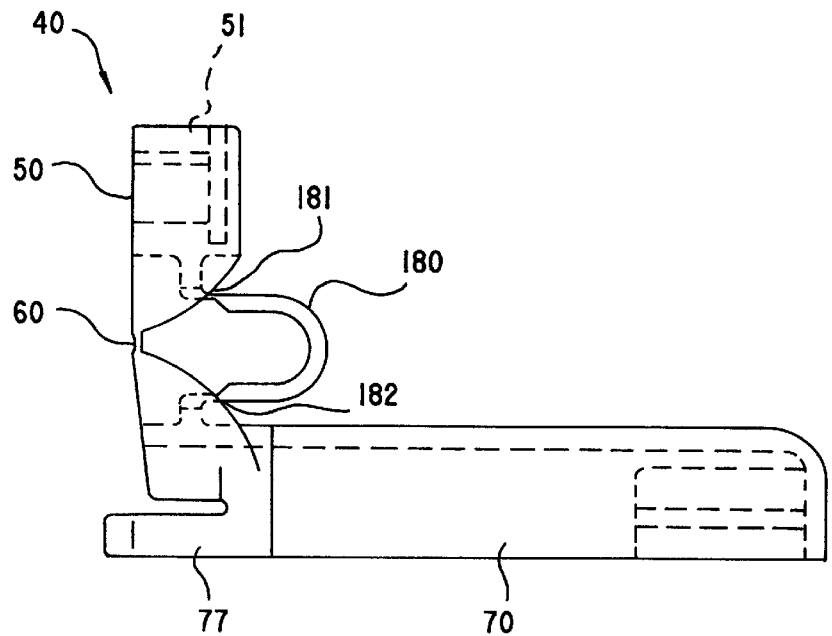

As shown in FIG. 17 and FIG. 18, the hinge portion 60 has a thin wall structure and couples the lower end of the cap securing portion 50 with the lower end of the cap main body 70.

As shown in FIG. 21, the cap main body 70 includes an accommodating portion 71 for accommodating the needle 20 and a cut-out portion 72 which communicates with the accommodating portion 71 and into which the needle 20 can go and from which the neddle can be taken out.

As shown in FIG. 17, the cap main body 70 is formed to a hollow rectangular shape, the upper portion of which is opened in the logitudinal direction and the entire length thereof is set longer than the needle 20.

Figure 19:
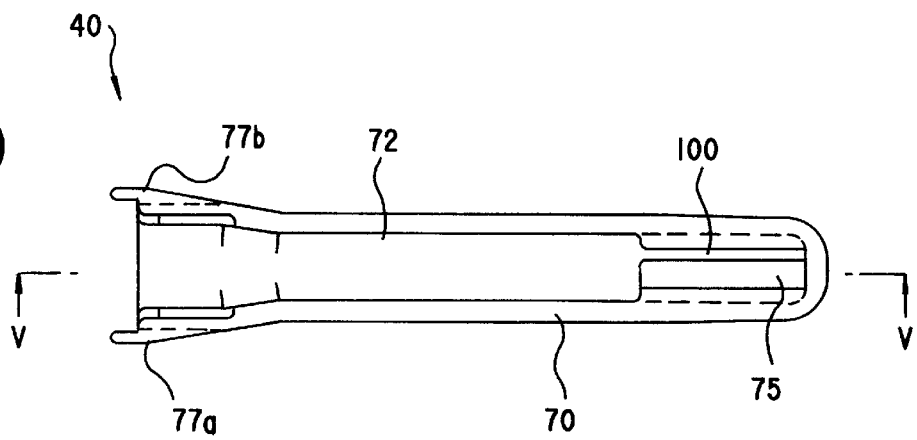

More specifically, the cap main body 70 has a groove formed to the interior thereof as shown in FIG. 17 and FIG. 19, the groove having an U-shaped cross section with its upper surface opened. The groove has a width set greater than the diameter of the needle 20 as well as an entire length set longer than the needle 20. The interior of the groove of the cap main body 70 is arranged as the accommodating portion 71 for accommodating the needle 20 and the upper open surface of the groove is arranged as a cut-out portion 72 into and from which the needle 20 can go and from which the needle can be taken out. Further, the cut-out portion 72 is formed to a long rectangular shape in the axial direction of the needle 20.

Figure 23:
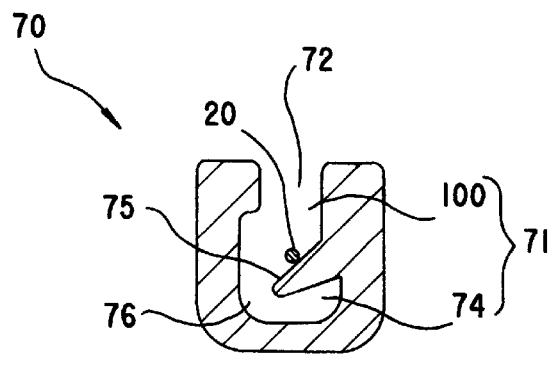

As shown in FIG. 23, the interior of the accommodating portion 71 is divided into two portions or a vacant accommodating portion used when needle is not used (hereinafter, simply referred to vacant accommodating portion 100) which faces to the cut-out portion 72 and accommodates the unused needle 20 and a vacant accommodating portion used when the needle is disposed of (hereinafter, simply referred to vacant accommodating portion 74) which communicates with the vacant accommodating portion 100 and accommodates the needle 20 after it is used, and the accommodating portion 71 has a projection 75 projecting therein. Both the vacant accommodating portions 100, 74 communicate with each other through a communicating passage 76 through which the needle 20 can pass.

As shown in FIG. 23, the projection 75 laterally projects to form a triangular shape and has an upper surface inclining downward to a free end. As a result, the used needle 20 goes down while being guided by the upper taper surface of the projection 75 and drops onto the bottom of the accommodating portion 71, that is, onto the vacant accommodating portion 74.

Figure 24:
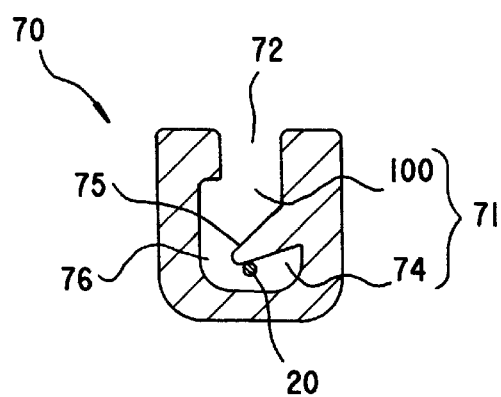

Whereas, the lower surface of the projection 75 is formed to a reverse taper surface which inclines downward to the free end as shown in FIG. 24. Thus, the used needle 20 which reaches the terminal end of the vacant accommodating portion 74 and then goes thereinto is difficult to go out from the vacant accommodating portion 74 because the exit of the vacant accommodating portion 74 is narrowed by the reversely tapered lower surface of the projection 75.

Note, although the projection 75 projects to form the triangular shape in the embodiment shown in the drawings, it may project to form a rectangular shape or a semicircular shape.

Further, a spring means 180 is formed between the cap securing portion 50 and the cap main body 70 as shown in FIG. 18 and FIG. 20. The spring means urges the cap main body 70 to a direction in which the cap main body 70 is secured to the cap securing portion 50 at a position for use (refer to FIG. 16) where the needle 20 is exposed by turning the cap main body 70 on the above hinge portion 60 as well as urges the cap main body 70 toward the direction where the needle 20 is located in the accommodating portion 71 when the cap main body 70 is reversed on the hinge portion 60.

As shown in FIG. 20, the above spring means is composed of a spring hinge 180 bent to a U-shape across the hinge portion 60. The spring hinge 180 has an end coupled with the cap securing portion 50 through a thin wall portion 181 and the other portion coupled with the cap main body 70 through a thin wall portion 182 as shown in FIG. 20.

Note, although the spring hinge 180 bent to the U-shape is used in the embodiment shown in the drawings as the spring means, the spring means is not limited to the spring hinge, the spring hinge 180 is not limited to the U-shape and any structure may be used so long as its urging direction is reversed in the midway of the opening and closing of the cap main body 70.

Further, as shown in FIG. 17, a stopper means 77 is formed between the cap securing portion 50 and the cap main body 70 to regulate the rotational angle of the cap main body 70 with respect to the cap securing portion 50 at the position where the cap main body 70 is closed.

In this embodiment, the above stopper means is formed to the cap main body 70, and more specifically it is composed of a pair of right and left stopper pieces 77a, extending rearward from both the right and left sides of the cap main body 70 toward the cap securing portion 50 as shown in FIG. 18 to FIG. 20.

As shown in FIG. 19, the right stopper piece 77a and left stopper piece 77b regulate the rotational angle of the cap main body 70 by the abutment of confronting inside stepped portions against the end surface of the cap securing portion 50.

Figure 25:
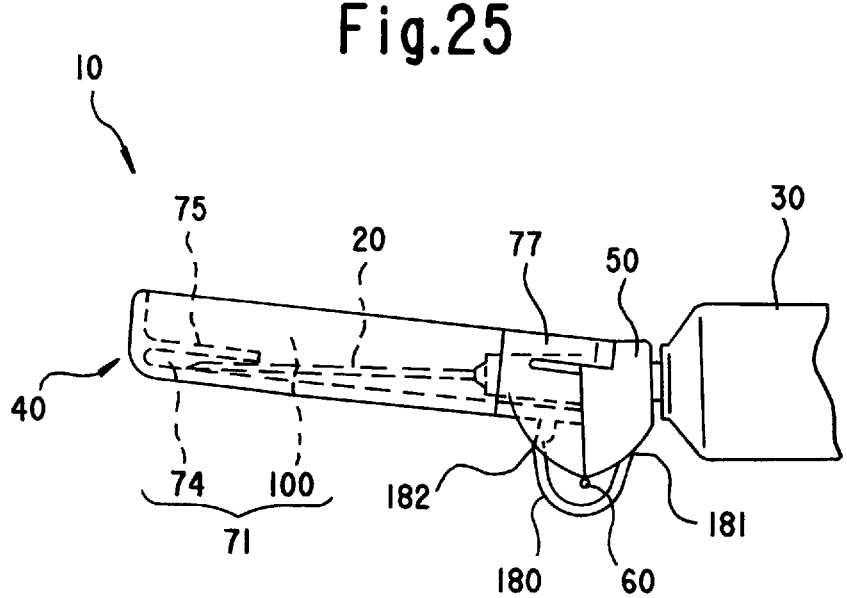
FIG. 25 corresponding to FIG. 16 is a plan view of a portion of the syringe in the disposal state.

As shown in FIG. 17, the unused needle 20 is accommodated in the vacant accommodating portion 100 in an unused state at the position where the rotational angle is regulated by the right and left stopper pieces 77a, 77b. When the cap main body 70 is opened and the needle 20 is used and then the cap main body 70 is closed again, the cap main body 70 stops once at the position where the stepped portions of the right and left stopper piece pieces 77a, 77b are abutted against the end surface of the cap securing portion 50. Thereafter, when the cap main body 70 is further rotated upward, the right and left stoppers 77a, 77b are pressed by the cap securing portion 50 and opened outside in the right and left directions against the elastic force of resin. As a result, the cap main body 70 is bent to a V-shape upward as shown in FIG. 25.

Note, although the right and left stopper pieces 77a, 77b are formed to the cap main body 70 as the stopper means in the embodiment shown in the drawings, it may be formed to the cap securing portion 50 side or the stepped portions formed to the inside surface of the stopper pieces 77a, 77b may be formed to the cap securing portion 50 side.

Next, a sequence for using the cap 40 arranged as described above will be described.

First, when the needle 20 is not yet used, the needle 20 is accommodated in the vacant accommodating portion 100 as shown in FIG. 17. Thus, the needle 20 is in a safe and sanitary state.

Next, when the needle 20 is to be used, it suffices only to pull the cap main body 70 toward the side where the hinge portion 60 exists, for example, downward while holding both the right and left sides of the cap main body 70.

Figure 16:
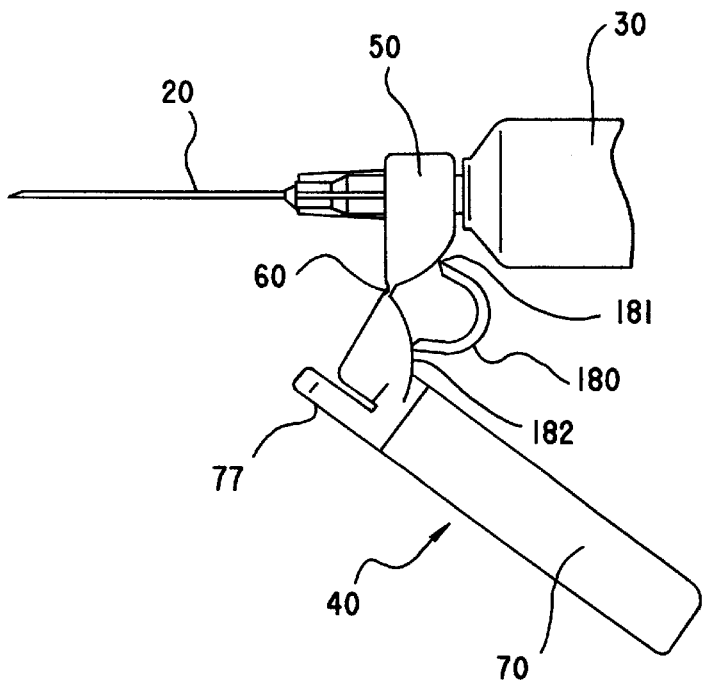
FIG. 16 is a plan view of a portion of the syringe showing the state that the cap main body is opened.

When the cap main body 70 is pulled downward, the cap main body 70 turns downward on the hinge portion 60 as shown in FIG. 16.

At the time, the interval between both the ends of the spring hinge 180 is increased. As a result, the restoring force of the spring hinge 180 applies an urging force for closing the cap main body 70 against the force for opening the cap main body 70.

Thus, when the cap main body 70 is to be opened, the cap main body 70 must be pulled against the urging force of the spring hinge 180.

When the cap main body 70 is opened to its midway position, the interval between both the ends of the spring hinge 180 is decreased on the contrary. As a result, the cap main body 70 is vigorously opened by the accumulated elastic force of the spring hinge 180 even if the force for pulling the cap main body 70 is released.

When the cap main body 70 is opened by the above operation, the spring hinge 180 returns to a stable state and the cap main body 70 is kept in the open state.

Therefore, the cap main body 70 can be kept in the open state and when the exposed needle 20 is used, the swing of the cap main body 70 can be prevented.

After the needle 20 is used, it is sufficient only to press the cap main body 70 toward the hinge portion 60 side thereof, for example, to press the lower surface thereof upward. When the cap main body 70 is pressed upward, the cap main body 70 turns upward and returns on the hinge portion 60 as shown in FIG. 25.

At the time, since the interval between both the ends of the spring hinge 180 is increased once, the cap main body 70 must be pressed upward against the urging force of the spring hinge 180. However, when the cap main body 70 is pressed upward up to its midway point, the interval between both the ends of the spring hinge 180 decreased accordingly.

As a result, even if the force for pressing the cap main body 70 upward, the cap main body 70 is vigorously closed by the accumulated elastic force of the spring hinge 180.

At the time, the used needle 20 gets into the vacant accomadating portion 100 through the cut-out portion 72 of the cap main body 70 as shown in FIG. 23.

When the cap main body 70 is further pressed upward, the used needle 20 goes down through the communicating passage 76 while being guided by the upper taper surface of the projection 75 and drops toward the bottom of the accommodating portion 71, that is, the vacant accommodating portion 74 as shown in FIG. 24.

Therefore, when the used needle 20 is disposed of, the used needle 20 goes to the inner part of the vacant accommodating portion 74 by being guided by the lower surface tapered reversely of the projection 75 when the cap main body 70 tends to open, thus the needle 20 is difficult to go out from the vacant accommodating portion 74.

Since the cap main body 70 is in the state that the upper portion thereof is bent upward with respect to the cap securing portion 50 as shown in FIG. 25, it can be easily determined from the outside appearance thereof that the cap main body 70 is already used.

Further, the operator can open and close the cap main body 70 while holding it, a hand does not get in touch with the vicinity of the tip of the used needle 20 or the tip does not face toward the direction of an operator. Thus, there is no possibility that the needle tip erroneously pierces or comes into contact with the hand of the operator, by which a safe and sanitary state can be achieved.

Figure 26:
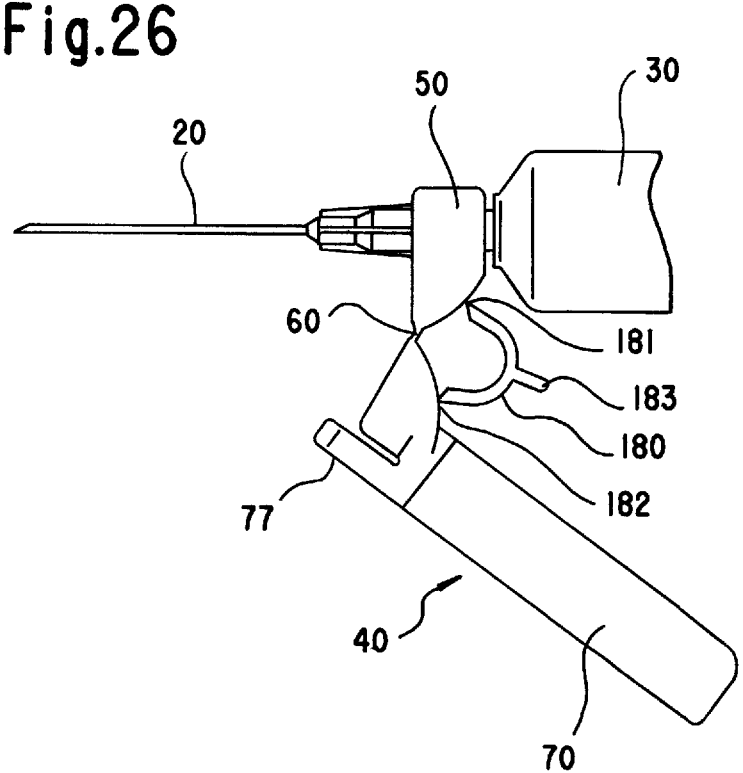
FIG. 26 a plan view of a portion of the syringe showing the state that the cap main body is locked to a disposal position.

FIG. 26 shows a fourth embodiment of the present invention and is a plan view of a portion of a syringe illustrating the state that a cap main body is opened.

The forth embodiment has a feature that an operating projection 183 is formed on a spring hinge 180 as shown in FIG. 26.

The operating projection 183 projects outward from the center of the outer periphery of the U-shaped portion of the spring hinge 180 to form a Y-shape as shown in FIG. 26.

According to the fourth embodiment, the operator can open and close cap main body 70 while holding the operating projection 183.

Note, the shape of the operating projection 183, the position where it is formed and the like are not limited to those of the fourth embodiment shown in FIG. 26 and the operating projection 183 may be formed to the cap main body 70 side.

Note, the respective embodiments shown in the present invention are only examples for illustration and do not restrict the present invention, thus the scope of the present invention is shown by claims to be described below and all the modifications contained in the scope of the claims are covered by the prevent invention

What is claimed is:

1. A syringe with a cap comprising:
    a syringe main body having a needle attached to an extreme end thereof;
    a cap for covering the needle of the syringe main body, wherein the cap includes a cap securing portion secured to the extreme end of the syringe main body, a cap main body pivotally coupled with the cap securing portion through a hinge portion, said cap main body including an accomodating portion for accomodating the needle and a cut-out portion which communicates with the accomodating portion and into which the needle can go and from which the needle can be taken out, and a breakable breaking portion interposed between said cap securing portion and said cap main body for securing said cap main body to said cap securing portion in a position where said needle is unused and is located in said accomodating portion and which is breakable for pivoting said cap main body on said hinge portion to a position for use; and securing means capable of securing said cap to said cap securing portion when said syringe is used.

2. A syringe with a cap according to claim 1, wherein said securing means comprises first locking means for locking said cap during use and said first locking means is interposed between said cap securing portion and said cap main body and locks said cap main body to said cap securing portion at a position for use where said needle is exposed when said cap main body is pivoted on said hinge portion from an accomodating position where said needle is accomodated in the accomodating portion of said cap main body to said position for use.

3. A syringe with a cap according to claim 2, further comprising second locking means interposed between said cap securing portion and said cap main body for locking said cap for disposal when said cap main body is pivoted on on said hinge portion in a reverse direction from the position for use to thereby accomodate said used needle in said accomodating portion and lock said cap main body to said cap securing portion at a position for disposal that is different from said accomodating position.

4. A syringe with a cap according to claim 1, wherein said securing means is composed of spring means interposed between said cap securing portion and said cap main body, said spring means urging said cap main body toward a direction for securing said cap main body to said cap securing portion at the position for use where said needle is exposed by turning said cap main body on said hinge portion as well as urging said cap main body toward a position where said needle is located in said accommodating portion when said cap main body is turned in the reverse direction on said hinge portion.

5. A syringe with a cap according to claim 4, wherein the interior of the accommodating portion of said cap main body is divided into two portions of a vacant accommodating portion used when said needle is not used which faces to said cut-out portion and accommodates said unused needle and a second vacant accommodating portion used when said needle is disposed of which communicates with said vacant accommodating portion and accommodates said needle after it is used and said accommodating portion forms a projection projecting therein.

6. A syringe with a cap comprising:

a syringe main body having a needle attached to an extreme end thereof;

a cap for covering the needle of the syringe main body, wherein the cap includes a cap securing portion secured to the extreme end of the syringe main body and a cap main body pivotally coupled with the cap securing portion through a hinge portion, said cap main body including an accomodating portion for accomodating the needle and a cut-out portion which communicates with the accomodating portion and into which the needle can go and from which the needle can be taken out, wherein the interior of the accomodating portion of said cap main body is divided into two portions a first vacant accomodating portion used when the needle is not used which faces to said cut-out portion and accomodates said unused needle and a second vacant accomodating portion used when the needle is disposed of which communicates with said first vacant accomodating portion and accomodates said needle after it is used and said accomodating portion forms a projection projecting therein, and a breakable breaking portion interposed between said cap securing portion and said cap main body for securing said cap main body to said cap securing portion in a position where said needle is unused and is located in said accomodatina portion and which is breakable for pivoting said cap main body on said hinge portion to a position for use; and securing means capable of securing said cap to said cap securing portion when said syringe is used.

7. A syringe with a cap according to claim 6, wherein spring means is formed between said cap securing portion and said cap main body, said spring means urging said cap main body toward a direction for securing said cap main body to said cap securing portion at the position for use where said needle is exposed by turning said cap main body on said hinge portion.

* * * * *